United States Patent [19]

Tokumoto et al.

[11] Patent Number: 5,457,228
[45] Date of Patent: Oct. 10, 1995

[54] METHOD FOR PRODUCING LOWER ALKYL ACETATE

[75] Inventors: Yuichi Tokumoto, Yokohama; Kazuo Sakamoto, Zama; Kikuo Sasaki; Isoo Shimizu, both of Yokohama, all of Japan

[73] Assignees: Daicel Chemical Industries, Ltd.; Nippon Petrochemicals Company, Limited, both of Japan

[21] Appl. No.: 330,115

[22] Filed: Oct. 27, 1994

Related U.S. Application Data

[63] Continuation of Ser. No. 784,361, Oct. 29, 1991, abandoned.

[30] Foreign Application Priority Data

Oct. 31, 1990 [JP] Japan ................................ 2-294237
Oct. 31, 1990 [JP] Japan ................................ 2-294238

[51] Int. Cl.$^6$ .................................................. C07C 67/04
[52] U.S. Cl. ........................................................ 560/241
[58] Field of Search .................................................. 560/241

[56] References Cited

U.S. PATENT DOCUMENTS

| | | | |
|---|---|---|---|
| 2,678,332 | 5/1954 | Cottle | 560/247 |
| 3,922,294 | 11/1975 | Leupold et al. | 554/161 |
| 4,263,448 | 4/1981 | Leacock | 560/241 |
| 4,503,163 | 3/1985 | Chu | 502/183 |

FOREIGN PATENT DOCUMENTS

| | | |
|---|---|---|
| 48-13345 | 2/1973 | Japan. |
| 2041364 | 9/1980 | United Kingdom. |

OTHER PUBLICATIONS

John H. Perry, Ph.D., Chemical Engineers' Handbook (1950) McGraw Hill Book Company, Inc., pp. 329–330.

*Primary Examiner*—José G. Dees
*Assistant Examiner*—Joseph M. Conrad
*Attorney, Agent, or Firm*—Scully, Scott, Murphy & Presser

[57] ABSTRACT

A method for producing a lower alkyl acetate in which undesirable polymerization of the starting material of olefin and deterioration of catalyst can be avoided, a higher catalytic efficiency and a higher reaction rate are attained, the installation of reaction equipment is inexpensive and the operation of the reaction can be carried out without difficulty. The method of the invention comprises the steps of feeding acetic acid and an olefin both in a liquid state and in cocurrent through a continuous flow type fixed bed reactor containing an acidic ion exchange resin catalyst(s) under the conditions that the molar ratio of acetic acid to the olefin in a feed current is in the range of 1.0 to 2.0 and an LHSV of acetic acid relative to the catalyst layer is 0.1 to 10.0 with maintaining the inlet of the catalyst bed at 70° C. to 120° C.; cooling the obtained reaction mixture to a temperature not lower than 70° C.; and recycling it to the catalyst bed.

8 Claims, 2 Drawing Sheets

METHOD FOR PRODUCING LOWER ALKYL ACETATE

This is a continuation of application Ser. No. 07/784,361, filed on Oct. 29, 1991, now abandoned.

BACKGROUND OF THE INVENTION

(1) Field of the Invention

The present invention relates to a method for producing lower alkyl acetates. More particularly, the invention relates to a method for continuously producing lower alkyl acetates such as isopropyl acetate and sec-butyl acetate by adding lower olefins to acetic acid in the presence of an acidic ion exchange resin catalyst. The lower alkyl acetates prepared by the method of the present invention are useful as solvents and as materials for preparing perfumes.

(2) Description of Prior Art

It is well known that, when acetic acid is allowed to react with an olefin using an acidic ion exchange resin catalyst, a corresponding alkyl acetate is obtained. For example, in the case that the olefin is propylene, isopropyl acetate is obtained through the following chemical equation:

In the case that an olefin of 1-butene or 2-butene is used, sec-butyl acetate is obtained through the following chemical equations (Japanese Patent Laid-Open Publication (Kokai) Nos. 49-100016 and 55-102530):

Concerning the above esterification, liquid phase reaction, gas phase reaction and gas-liquid mixed phase reaction are known in view of the types of reaction. The gas phase reaction is not desirable in industrial practice because the polymerization of olefin on the catalyst, which disadvantageously reduces the effect and life of catalyst, cannot be avoided. Japanese Patent Publication (Kokoku) No. 59-44295 discloses gas-liquid phase reaction in which liquid phase acetic acid and gas phase propylene are cocurrently mixed. In this reaction, the catalytic efficiency can be improved because the liquid acetic acid moistens the surfaces of catalyst particles, and as a result, it is possible to carry out the reaction under moderate conditions. This can be applied to the reaction using other olefins such as linear butenes or the like.

However, because a gas phase olefin is passed through a layer of catalyst, the disadvantage that the catalytic efficiency is inevitably lowered, cannot be avoided. Furthermore, in the case of gas-liquid mixed phase reaction, the olefin dissolved in acetic acid is considered to participate in the reaction. When an olefin dissolved in a liquid phase is consumed through the reaction in esterification, the gas phase olefin must be additionally dissolved into the liquid phase, which takes a lot of time. Therefore, the liquid phase reaction in which both the acetic acid and an olefin are used in a liquid phase, is preferable in the industrial practice.

With regard to the mode of reaction in the above esterification, continuous process is more advantageous than batchwise process in view of industrial practice. In the case of continuous process, a continuous vessel-type reactor, a flow-type fixed bed reactor, a moving bed-type reactor, and a fluidized bed-type reactor are used. In view of the cost required of the apparatus and maintenance, a fixed bed continuous tubular reactor is most desirable. Nevertheless, in the reactor of this type in an industrial scale, the temperature rise inevitably occurs along the stream of reactants because the above reaction is intensely exothermic. Therefore, the rate of reverse reaction to decompose the produced alkyl acetate into acetic acid and an olefin is increased. For this reason, not only the final conversion ratio of olefin cannot be raised but also it was found out that the catalytic activity, especially the activity of ion exchange resin catalyst, is lost. Accordingly, in order to attain a high conversion ratio of olefin and a high catalytic activity, it is necessary to control properly the temperature distribution in the reaction zone.

For example, a multi-tube fixed bed reactor is disclosed in European Patent Publication No. 0 054 576 A1. When the above reaction is carried out in a gas-liquid mixed phase or liquid phase using a complicated multi-tube fixed bed reactor, it is not desirable that the cost for the reaction equipment is high because the reactor must be sufficiently resistant to pressure. In addition, the maintenance operation such as change of catalyst and so forth is quite troublesome.

Accordingly, development of an easy and inexpensive method for controlling reaction temperatures is eagerly wanted in order to carry out the above esterification using a single tube fixed bed reactor which is advantageous in view of the cost and maintenance.

BRIEF SUMMARY OF THE INVENTION

In order to solve the above problems in the conventional art, the inventors of the present application have carried out extensive investigation. As a result, the present invention was accomplished.

It is therefore an object of the present invention to provide an improved method for producing lower alkyl acetates.

Another object of the present invention is to provide a method for producing lower alkyl acetates in which undesirable polymerization of olefin and deterioration of catalyst can be avoided in the esterification.

A further object of the present invention is to provide a method for producing lower alkyl acetates in which a higher catalytic efficiency and a higher reaction rate are attained.

Still a further object of the present invention is to provide a method for producing lower alkyl acetates in which the installation of reaction equipment is inexpensive and the operation of the reaction can be carried out without difficulty.

That is, the present invention relates to a method for producing a lower alkyl acetate comprising the steps of feeding acetic acid and an olefin both in a liquid state and in cocurrent through a continuous flow type fixed bed reactor containing a styrene-sulfonic acid type ion exchange resin catalyst and/or a phenol-sulfonic acid type ion exchange resin catalyst under the conditions that the molar ratio of acetic acid to olefin (acetic acid/olefin) in a feed current is in the range of 1.0 to 2.0 and an LHSV of acetic acid relative to the catalyst layer is 0.1 to 10.0 with maintaining the temperature of the inlet of the catalyst bed in the range of 70° C. to 120° C., cooling the obtained reaction mixture to a temperature not lower than 70° C., and recycling it to the catalyst bed.

In the case that the olefin is propylene to produce isopropyl acetate, the ratio of recycling can be defined by the following equation (I):

$$\frac{7.9A + 4.9}{3.7A^2 + 1.17A - 1} \leq X \quad (I)$$

wherein the symbol X means the ratio by weight of the quantity of recycled current to the quantity of feed current and A is the molar ratio of acetic acid to propylene in the feed current. The resultant value on the left side of the above equation is sometimes referred to as "calculated recycling ratio".

Furthermore, in the case that the olefin is linear butenes such as 1-butene and 2-butene to produce sec-butyl acetate, more preferable controlling of reaction can be attained with the conditions that the temperature of the inlet of the catalyst bed is maintained in the range of 80° C. to 120° C., the reaction mixture obtained is cooled to a temperature not lower than 80° C., and the ratio of recycling to the catalyst bed is a value defined by the following equation (II):

$$\frac{7.6A + 5.9}{3.6A^2 + 1.5A - 1} \leq X \quad (II)$$

wherein the symbol X also means the ratio by weight of the quantity of recycled current to the quantity of feed current and A is the molar ratio of acetic acid to the linear butene in the feed current. The resultant value on the left side of the above equation is sometimes referred to as "calculated recycling ratio".

The evolution of heat in the reaction of the present invention is vigorous beyond comparison with the gas-liquid phase reaction because the reaction of the invention is a liquid phase reaction. When the temperature of reaction is high, the reaction proceeds rapidly, however, the reverse reaction also occurs. Furthermore, in higher temperatures, the catalytic function is impaired. Because of these factors, the reaction temperature must be controlled within an adequate range. However, when the temperature of reaction is simply lowered, the rate of reaction is reduced, which is not desirable in view of industrial production.

In the present invention, therefore, the method of recycling, of a portion of reaction mixture was adopted. However, according to the experiments carried out by the present inventors, when the recycling is simply done in a single tube reactor, the uneven distribution of temperature in a catalyst bed could not be avoided to occur. Because of the use of a single tube reactor, the cooling operation is done by simple external cooling. Without saying, the generation of heat of reaction is related to the quantities of reactants and the molar ratio of them and the temperature is the factors of catalytic efficiency. Accordingly, it is considered that only a simple recycling method cannot be adopted herein. It should be noted that, for the practical or industrial scale, it is difficult to determined previously the reaction conditions by means of a computer or the calculation according to chemical engineering technique.

The inventors of the present application have carried out extensive investigation with regard to the above case using the ion exchange resin catalysts of styrenesulfonic acid type and phenol-sulfonic acid type resin. As a result, it was found out that the above reaction can be carried out with an industrially acceptable reaction efficiency by adopting a value which is calculated using the mass ratio of the acid and the olefin used. In addition, it was also found out that the deterioration of catalytic efficiency is low in this method.

BRIEF DESCRIPTION OF THE DRAWINGS

These and other objects and features of the present invention will become more apparent from the following description and examples taken in connection with the accompanying drawings in which.

DETAILED DESCRIPTION OF THE INVENTION

In the following, the present invention will be described in more detail.

The term "olefin" herein referred to means those having 2 to 5 carbon atoms, and more preferably those having 3 or 4 carbon atoms such as propylene and linear butenes of 1-butene and 2-butene.

The term "lower alkyl" herein referred to with regard to the products of lower alkyl acetates, means alkyl groups having 2 to 5 carbon atoms, and more preferably those having 3 or 4 carbon atoms such as isopropyl group and sec-butyl group.

The term "acidic ion exchange resin" herein referred to is an ion exchange resin which exhibits an acidic property, such as styrene sulfonic acid type resin and phenol sulfonic acid type resin. The styrene sulfonic acid type ion exchange resin is made by copolymerizing styrene with a polyunsaturated compound such as divinyl-benzene to obtain a resin which is followed by sulfonation. The phenol sulfonic acid type ion exchange resin is generally made by condensing phenol sulfonic acid with formaldehyde.

More particularly, these ion exchange resin catalysts may be those which are available in the market. For example, a commercially available catalyst of the styrene-sulfonic acid type cation exchange resin which is suitable for the purpose of the invention has a basic structure of styrene/divinylbenzene macroporous copolymer. A preferable cation exchange resin has a content of divinylbenzene in the range of 1 to 50 wt. %, preferably 2 to 40 wt. %, a particle diameter in the range of 0.1 to 10 mm and an acid value in the range of 0.05 to 20 meq/g.

As a source for the olefin used in the present invention may be a mixture of hydrocarbons containing at least 20% or more of the relevant olefin.

For example, as a source for the propylene used in the present invention is a mixture of hydrocarbons containing 20% by weight or more propylene. Advantageously used as such a propylene source is a $C_3$ fraction containing propylene which is obtained by catalytically cracking petroleum such as naphtha. In order to suppress the evolution of heat in reaction in the method of the present invention, it is desirable to use the above-mentioned $C_3$ fraction (hereinafter referred to as "FCC propylene").

This FCC propylene contains hydrocarbons having 3 carbon atoms such as propylene and propane as well as trace quantities of olefins besides $C_3$ olefins, heavy metals and sulfur. Accordingly, it is apprehended that olefins besides those having 3 carbon atoms react with acetic acid and produce impurities which lower the purity of unreacted acetic acid and the product of isopropyl acetate or heavy metals and sulfur accelerate the deterioration of catalyst. However, these disadvantages do not occur as described in the following examples of the present invention.

Furthermore, as a source for the linear butene used in the present invention is also a mixture of hydrocarbons containing 20% by weight or more linear butene. Advantageously used as such a linear butene source is a $C_4$ fraction containing linear butene which is obtained by thermally cracking petroleum such as naphtha, that is the so-called spent-spent BB fraction which is obtained by removing butadiene and isobutylene. In order to suppress the evolution of heat in the reaction according to the method of the present invention, it is desirable to use the above-mentioned spent-spent BB fraction (hereinafter sometimes referred to as "S/S butene").

This S/S butene contains hydrocarbons having 4 carbon atoms such as linear butene and linear butane as well as trace quantities of olefins and diolefins besides the hydrocarbons having 4 carbon atoms. However, the disadvantage caused by the reaction of these olefins besides those having 4 carbon atoms with acetic acid to produce impurities does not caused to occur as described in the following examples.

The molar ratio of "acetic acid/olefin" in the feed current that is newly fed into a catalyst bed (hereinafter referred to as simply "feed current"), is 1.0 to 2.0, more preferably 1.2 to 2.0. When this molar ratio is lower than 1.0, side reactions such as the polymerization of olefin increase, which is undesirable in view of economy. On the other hand, when the molar ratio is higher than 2.0, the quantity of unreacted acetic acid increases, which increases the expenses necessary for the recovering process such as distillation. The olefin and acetic acid can be fed into a reactor either separately or as a mixture of them so long as the above molar ratio is maintained. By the way, it is to be noted that the above-mentioned feed current means the one which does not contain the later-mentioned recycled current. Accordingly, the acetic acid and olefin in the above molar ratio does not include the components derived from the recycled current.

The quantity of feed current to the catalyst bed is preferably 0.1 to 10, more preferably 0.2 to 5, as LHSV of acetic acid relative to a catalyst bed. A value of LHSV smaller than 0.1 is not desirable because the production efficiency is too low. On the other hand, an LHSV larger than 10 is not desirable either because the average retention time necessary for reaction in a catalyst bed cannot be secured and a larger LHSV lowers the ratio of conversion.

The reaction pressure in a reactor in the method of the present invention may be a value which is sufficient for maintaining the reaction system in a liquid state. For example, in the case that propylene is used as the olefin, a value of pressure can be selected from the range of 15 kg/cm$^2$ to 100 kg/cm$^2$, preferably 15 kg/cm$^2$ to 50 kg/cm$^2$. In the case that butene is used as the olefin, a value of pressure can be selected from the range of 5 kg/cm$^2$ to 100 kg/cm$^2$, preferably 5 kg/cm$^2$ to 50 kg/cm$^2$. When a reaction pressure is lower than the lower limit, a gas phase portion undesirably occurs in the reaction system. On the other hand, when a reaction pressure is higher than the upper limit, it is not economical because it necessitates unduly high pressure-resistant equipment.

The reaction according to the present invention is exothermic reaction. In order to put this reaction into practice by flow type fixed bed reactor, the inventors of the present invention have found out that the controlling of temperatures in reaction zones is important, thereby accomplishing the present invention.

That is, the reaction temperature near the inlet of the catalyst bed of a reactor must be in the range of 70° to 120° C. As described in the foregoing paragraph, the reaction according to the present invention is exothermic reaction, however, because the above temperature defines the temperature near the inlet of catalyst bed, the controlling of temperature in order to maintain the above temperature range can easily be attained by properly heating or cooling with considering the use of recycled current. When linear butenes are used as starting materials, the lower value in the above temperature range is preferably raised to 80° C. In the case that the temperature near the inlet of catalyst bed is lower than the lower limit of the above temperature range, it is not desirable because the rate of reaction is too low even if the temperature of succeeding catalyst bed is set high. On the other hand, when the temperature is higher than the upper limit of 120° C., the rate of reverse reaction to decompose the lower alkyl acetate into acetic acid and an olefin is raised. This is not desirable because not only the ratio of conversion of olefin cannot be raised but also side reactions such as polymerization of olefin increases.

In the present invention, it is important to control the temperature of a reaction zone by cooling a certain quantity of at least a part of reacted mixture as a reaction product passed from the catalyst bed with a proper heat-removing device such as a heat exchanger and by recycling it to the reaction zone. In the recycling, it is not particularly necessary to remove unreacted components and the aimed lower alkyl acetate from the reaction product obtained out of the reactor.

The temperature of recycled current supplied through a proper heat-removing device is naturally lower than the reaction product at the outlet of catalyst bed because the former is fed after being cooled. The temperature of cooling must be at a value above the temperature near the inlet of catalyst bed, that is, the cooling temperature is not lower than 70° C. The temperature of the recycled current lower than this level is not desirable because the temperature of catalyst bed receiving the recycled current is lowered.

In the present invention, the quantity of recycling necessary for the controlling of reaction temperature depends upon the heat generation, the allowable range of temperature rise in the reaction zone and the release of heat from the reaction zone. Furthermore, the degree of heat generation depends upon the feed rate and the molar ratio of acetic acid to olefin of the feed current.

The inventors of the present application have carried out extensive investigation concerning these complicated factors. As a result, it was found out that appropriate temperature controlling can be attained when the recycling ratio X (hereinafter sometimes referred to as "actual recycling ratio") exceeds 2 and in the case that the starting olefin is $C_3$ or $C_4$ olefin, the actual recycling ratio exceeds the value of the left side of the foregoing equations (I) or (II) with a variable of molar ratio A, thereby accomplishing the present invention. It has never been anticipated that the recycling ratio can be defined only by the molar ratio A of acetic acid to the olefin in the feed current.

The upper value of the actual recycling ratio is not limited, however, too large quantity of recycling is not desirable because it requires a lot of costs for equipment and energy for recycling. In practical operation, the recycling ratio is at the most 100.

Figure 1:
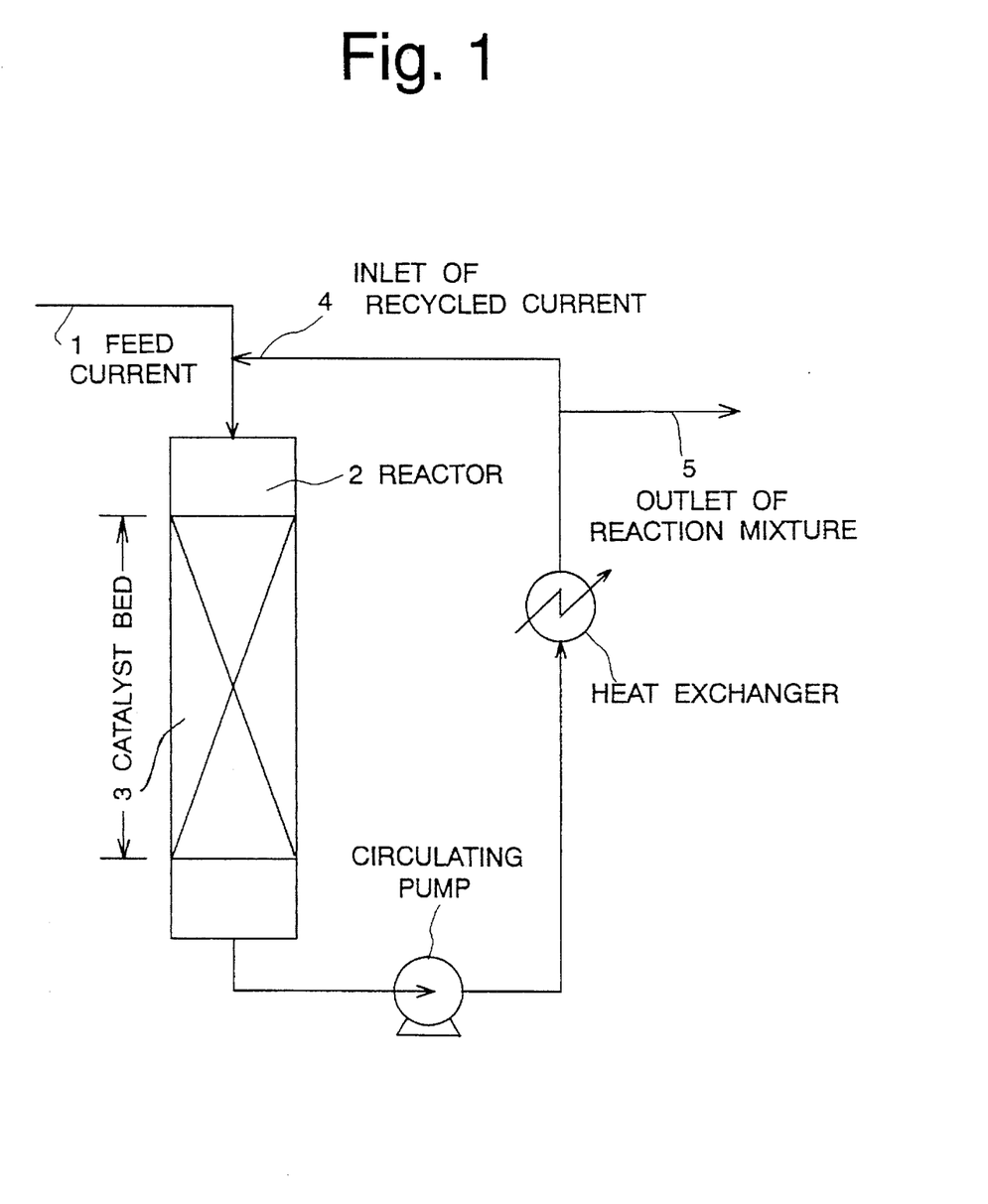
FIG. 1 is a flow sheet of an embodiment of a reactor used in the method of the present invention.

In the present invention, the location in the catalyst bed to receive the recycled current is not limited. For example, as shown in FIG. 1, it is possible to recycle it by joining it with a feed current at the inlet of a reactor.

Figure 2:
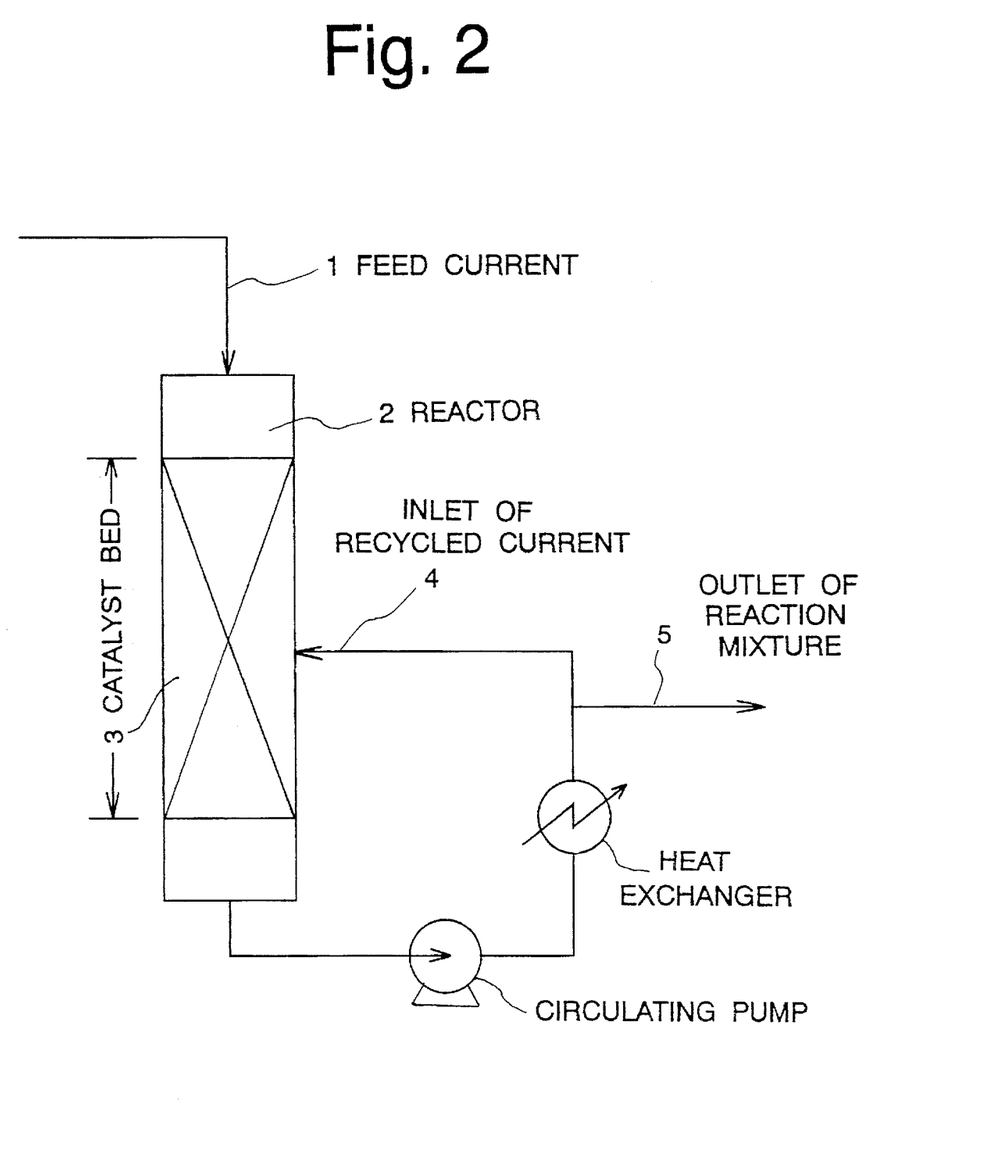
FIG. 2 is also a flow sheet of another embodiment of a reactor used also in the method of the present invention.

However, in order to facilitate to raise the effect of temperature controlling by the recycling operation, for example, as shown in FIG. 2, the recycled current can be fed into the middle portion of the catalyst bed. In this case, assuming that V is the volume of catalyst bed from the inlet of recycled current to the outlet of catalyst bed, the value of V is desirably one-tenth or more relative to the total volume of the catalyst bed. When the recycled current is introduced into a downstream side of that position, the recycled current cannot be dispersed sufficiently in the catalyst bed and stable controlling of temperature cannot be attained.

The present invention was described with a one-stage reactor, however, reactors of two or more stages in series can also be used under the above conditions. In the case of a plurality series of reactors, the above-mentioned feed current and the temperature of the inlet of catalyst bed respectively mean values in a first reactor in which the reaction is initiated. Furthermore, the volume of catalyst bed in the description about the location of introducing the recycled current means the total volume of catalyst beds in a plurality of reactors.

Incidentally, the aimed highly pure lower alkyl acetates such as isopropyl acetate and sec-butyl acetate can easily be obtained by distilling a portion of reaction mixture.

In order that those skilled in the art may better understand the present invention and the manner in which it may be practiced, the present invention will be described in more detail with reference to examples.

The composition of FCC propylene used in the following examples is: 76.1% by weight of propylene and 22.0% by weight of propane. The composition of S/S butene is: 64.3% by weight of linear butene and 35.2% by weight of butane. The molar ratio means the ratio of acetic acid to the above olefins and LHSV is expressed on the basis of the feed rate of acetic acid.

EXAMPLE 1

Ten liter of an acidic ion exchange resin catalyst of LEWATIT SPC 118 (H-type, trademark, made by Bayer A. G.) was packed in the middle portion of a circular tube made of stainless steel of 2 m in length and 10 cm in diameter. The ion exchange resin catalyst was a product prepared by sulfonating a styrene-divinylbenzene copolymer. The remained space in the reactor was filled with porcelain Raschig rings, thereby preparing a continuous flow fixed bed reactor.

This reactor was put vertically in a thermostat maintained at 85° C. to prepare a device as shown in FIG. 1, in which the thermostat is not shown.

A liquid feed current 1 consisting of acetic acid and propylene was fed into a reactor 2 and allowed to react in a catalyst bed 3. A reaction mixture was then taken out through a circulating pump. The reaction mixture was cooled by a heat exchanger and a part of the reaction mixture was recycled to a recycled current inlet 4. The recycled current was joined together with the feed current 1 at the recycled current inlet 4. The remainder of the reaction mixture was continuously taken out from a reaction mixture outlet 5.

A feed current of 1.0 in LHSV of acetic acid and 1.43 in molar ratio of acetic acid to propylene (95 wt. % purity) was fed into this reactor at a reaction pressure of 40 kg/cm². The recycled current was cooled to 85° C. by the heat exchanger and recycled from the inlet of catalyst bed at an actual recycling ratio of 12 (the above-mentioned calculated recycling ratio according to the equation (I) was 2.0). In this step, the temperature distribution in the catalyst bed was raised evenly and the temperatures of the inlet and outlet of the catalyst bed were 85° C. and 92° C., respectively.

The effluent reaction mixtures were analyzed every 5 hours by gas chromatography. After the composition became stable in a steady state, the conversion ratio of propylene was 89.8 mole % and the selectivity to isopropyl acetate was 96.6 mole %. After the reaction was continued for 1,000 hours, the activity of catalyst was hardly changed giving similar values in conversion ratio and selectivity.

EXAMPLE 2 to 5

In the same apparatus as the one in Example 1, the catalyst was changed to an acidic ion exchange resin catalyst of AMBERLYST-15 (H-type, trademark, made by Rohm & Haas Corp.) which was prepared also by sulfonating a styrene-divinylbenzene copolymer. Using FCC propylene as a starting material, reaction was carried out in the similar manner as in Example 1 except that the temperature of the inlet of catalyst bed, molar ratio, LHSV, reaction pressure and actual recycling ratio were varied, respectively.

Results obtained are shown in the following Table 1. The deterioration of catalytic activity was not observed in any of the examples.

TABLE 1

| | Example | | | |
|---|---|---|---|---|
| Items | 2 | 3 | 4 | 5 |
| Reaction Pressure (kg/cm²) | 30 | 25 | 30 | 50 |
| L H S V | 0.2 | 2.0 | 10.0 | 5.0 |
| Molar Ratio | 1.0 | 2.0 | 2.0 | 1.5 |
| Temp. of Thermostat (°C.) | 70 | 80 | 100 | 120 |
| Calculated Recycling Ratio | 3.3 | 1.3 | 1.3 | 1.8 |
| Actual Recycling Ratio | 20.0 | 5.5 | 3.0 | 11.5 |
| Temp. of Inlet of Catalyst Bed (°C.) | 70 | 80 | 100 | 120 |
| Temp. of Outlet of Catalyst Bed (°C.) | 76 | 90 | 114 | 128 |
| Conversion Ratio of Propylene (mole %) | 89.7 | 93.9 | 91.1 | 84.3 |
| Selectivity to Isopropyl Acetate (mole %) | 97.5 | 98.8 | 92.4 | 90.8 |

EXAMPLE 6 and 7

The reaction was carried out in the similar manner as in Example 3 except that the inlet of recycled current to a catalyst bed was changed as shown in FIG. 2, in which a thermostat is not shown.

In FIG. 2, the liquid feed current 1 consisting of acetic acid and propylene was fed into a reactor 2 and it was allowed to react in a catalyst bed 3. The reaction mixture was taken out through a circulating pump. The reaction mixture was then cooled by a heat exchanger and a part of the cooled reaction mixture was fed as a recycled current into a recycled current inlet 4 in the middle portion of the catalyst bed 3. The remainder portion of the reaction mixture was continuously taken out from a reaction mixture outlet 5.

The results obtained by using the reactor in FIG. 2 are shown in Table 2. No deterioration in catalytic activity was observed.

TABLE 2

| Items | Example 6 | Example 7 |
|---|---|---|
| Reaction Pressure (kg/cm$^2$) | 25 | 25 |
| L H S V | 2.0 | 2.0 |
| Molar Ratio | 2.0 | 2.0 |
| Temp. of Thermostat (°C.) | 80 | 80 |
| Calculated Recycling Ratio | 1.3 | 1.3 |
| Actual Recycling Ratio | 5.5 | 5.5 |
| Location of Recycling | 0.5 | 0.25 |
| Temp. of Inlet of Catalyst Bed (°C.) | 80 | 80 |
| Temp. of Inlet for Recycled Current (°C.) | 83 | 87 |
| Temp. of Outlet of Catalyst Bed (°C.) | 92 | 111 |
| Conversion Ratio of Propylene (mole %) | 93.2 | 86.8 |
| Selectivity to Isopropyl Acetate (mole %) | 94.7 | 91.5 |

(Remark)
Location of Recycling:
The value of the volume of catalyst bed from the point of introduction of recycled current to the outlet of catalyst bed divided by the total volume of the catalyst bed.

Comparative Example 1

Reaction was carried out in the similar manner as in Example 2 except that the reaction mixture was not recycled.

As a result, the temperature in the reactor was raised rapidly and the temperature of the outlet was above 180° C. As much sulfur dioxide was detected at the outlet of the reactor, the reaction was stopped. The catalyst bed was checked up and it was found that the pale brown catalyst before the reaction was changed to black and the acidic activity was almost lost.

Comparative Example 2 and 3

Reaction was carried out in the similar manner as in Examples 4 and 5 except that the actual recycling ratios were changed.

The results obtained are shown in Table 3. In any Examples, the catalytic activity was lost within several minutes to several hours.

TABLE 3

| Items | Comparative Example 2 | Comparative Example 3 |
|---|---|---|
| Reaction Pressure (kg/cm$^2$) | 30 | 50 |
| L H S V | 10.0 | 5.0 |
| Molar Ratio | 2.0 | 1.5 |
| Temp. of Thermostat (°C.) | 100 | 120 |
| Calculated Recycling Ratio | 1.3 | 1.8 |
| Actual Recycling Ratio | 0.5 | 1.0 |
| Temp. of Inlet of Catalyst Bed (°C.) | 100 | 120 |
| Temp. of Outlet of Catalyst Bed (°C.) | 144 | 166 |
| Conversion Ratio of Propylene (mole %) | 76.0 | 64.1 |
| Selectivity to Isopropyl Acetate (mole %) | 72.2 | 60.7 |

EXAMPLE 8

Preparation of sec-butyl acetate was carried out in the similar manner as in Example 1 except that a feed current of 1.8 in molar ratio of acetic acid to linear butene (purity: 99 wt.%) was fed at a reaction pressure of 20 kg/cm$^2$ and the recycling ratio of 15 (the foregoing calculated recycling ratio according to the equation (II) was 1.5). In this step, the temperature distribution in the catalyst bed was raised evenly and the temperature of the inlet and the outlet of the catalyst bed were 85° C. and 89° C.

The effluent reaction mixtures were analyzed every 5 hours by gas chromatography. After the composition became stable in a steady state, the conversion ratio of linear butene was 86.2 mole % and the selectivity to sec-butyl acetate was 94.3 mole %. After the reaction was continued for 1,000 hours, the activity of catalyst was hardly changed giving similar values in conversion ratio and selectivity.

EXAMPLES 9 to 12

In the same apparatus as the one in Example 8, the catalyst was changed to an acidic ion exchange resin catalyst of AMBERLYST-15 (H-type, trademark, made by Rohm & Haas Corp.). Using S/S butene as a starting material, reaction was carried out in the similar manner as in Example 8 except that the temperature of the inlet of catalyst bed, molar ratio, LHSV, reaction pressure and actual recycling ratio were varied, respectively.

Results obtained are shown in the following Table 4. The deterioration of catalytic activity was not observed in any of the examples.

TABLE 4

| Items | Example 9 | Example 10 | Example 11 | Example 12 |
|---|---|---|---|---|
| Reaction Pressure (kg/cm$^2$) | 50 | 25 | 30 | 50 |
| L H S V | 0.2 | 2.0 | 10.0 | 5.0 |
| Molar Ratio | 1.0 | 2.0 | 2.0 | 1.5 |
| Temp. of Thermostat (°C.) | 80 | 90 | 100 | 120 |
| Calculated Recycling Ratio | 3.3 | 1.3 | 1.3 | 1.9 |
| Actual Recycling Ratio | 23.0 | 4.2 | 3.4 | 10.0 |
| Temp. of Inlet of Catalyst Bed (°C.) | 80 | 90 | 100 | 120 |
| Temp. of Outlet of Catalyst Bed (°C.) | 87 | 102 | 119 | 128 |
| Conversion Ratio of Linear Butene (mole %) | 68.6 | 82.9 | 80.5 | 75.4 |
| Selectivity to sec-Butyl Acetate (mole %) | 92.4 | 96.6 | 91.8 | 90.0 |

EXAMPLES 13 and 14

The reaction was carried out in the similar manner as in Example 10 except that the inlet of recycled current to a catalyst bed was changed as shown in FIG. 2.

In FIG. 2, the liquid feed current 1 consisting of acetic acid and linear butene was fed into a reactor 2 and it was allowed to react in a catalyst bed 3 and succeeding treatment was carried out in the similar manner as in Example 6. The results obtained are shown in Table 5. No deterioration in catalytic activity was observed.

TABLE 5

| Items | Example 13 | Example 14 |
| --- | --- | --- |
| Reaction Pressure (kg/cm$^2$) | 25 | 25 |
| L H S V | 2.0 | 2.0 |
| Molar Ratio | 2.0 | 2.0 |
| Temp. of Thermostat (°C.) | 90 | 90 |
| Calculated Recycling Ratio | 1.3 | 1.3 |
| Actual Recycling Ratio | 4.2 | 4.2 |
| Location of Recycling | 0.5 | 0.25 |
| Temp. of Inlet of Catalyst Bed (°C.) | 90 | 90 |
| Temp. of Inlet for Recycled Current (°C.) | 95 | 98 |
| Temp. of Outlet of Catalyst Bed (°C.) | 110 | 125 |
| Conversion Ratio of Linear Butene (mole %) | 81.2 | 79.7 |
| Selectivity to sec-Butyl Acetate (mole %) | 93.2 | 89.5 |

Comparative Example 4

Reaction was carried out in the similar manner as in Example 9 except that the reaction mixture was not recycled.

As a result, the temperature in the reactor was raised rapidly and the temperature of the outlet was above 180° C. As much sulfur dioxide was detected at the outlet of the reactor, the reaction was stopped. The catalyst bed was checked up and it was found that the pale brown catalyst before the reaction was changed to black and the acidic activity was almost lost.

Comparative Example 5 and 6

Reaction was carried out in the similar manner as in Examples 11 and 12 except that the actual recycling ratios were changed.

The results obtained are shown in Table 6. In any Examples, the catalytic activity was lost within several minutes to several hours.

TABLE 6

| Items | Comparative Example 5 | Comparative Example 6 |
| --- | --- | --- |
| Reaction Pressure (kg/cm$^2$) | 30 | 50 |
| L H S V | 10.0 | 5.0 |
| Molar Ratio | 2.0 | 1.5 |
| Temp. of Thermostat (°C.) | 100 | 120 |
| Calculated Recycling Ratio | 1.3 | 1.9 |
| Actual Recycling Ratio | 0.5 | 1.0 |
| Temp. of Inlet of Catalyst Bed (°C.) | 100 | 120 |
| Temp. of Outlet of Catalyst Bed (°C.) | 142 | 164 |
| Conversion Ratio of Linear Butene (mole %) | 63.4 | 52.8 |
| Selectivity to sec-Butyl Acetate (mole %) | 70.8 | 51.3 |

As will be understood from the above detailed description and several examples of the present invention, the efficient liquid phase reaction can be carried out using inexpensive fixed bed continuous tubular reactor. Furthermore, it was made possible to control the temperature distribution in the reaction zone and to attain stably the high conversion ratio of olefin and a high productivity of alkyl acetate. This process can be worked with economical advantage even when the mixed gas of olefin and paraffin which is separated from the reaction product is discarded intact, so that it is not necessary to recover, refine and compress the used olefinic material for the reuse. Accordingly, the cost for installation of equipment for such a treatment is much saved.

Still further, as will be understood from the above-described examples, because the selectivity to the alkyl acetate is sufficiently high, the variable costs can be reduced and the refining of the alkyl acetate and unreacted acetic acid is easy.

In addition, according to the method of the present invention, a complicated multi-tube reactor is not necessary but only a single tube reactor can be satisfactorily used. Furthermore, as a means for cooling the single tube reactor, any special device is not required but only a common externally cooling means is sufficient.

What is claimed is:

1. A method for producing isopropyl acetate comprising the steps of feeding acetic acid and propylene both in a liquid state and in cocurrent through a continuous flow type fixed bed reactor containing a styrene-sulfonic acid type ion exchange resin catalyst and/or a phenol-sulfonic acid type ion exchange resin catalyst under the conditions that the molar ratio of acetic acid to said propylene in the feed current is in the range of 1.0 to 2.0 and the LHSV of acetic acid relative to the catalyst is 0.1 to 10.0 while maintaining the temperature of the inlet of the catalyst bed in the range of 70° C. to 120° C.; cooling the obtained reaction mixture to a lower temperature which is lower than the temperature at the outlet of the catalyst bed and is not lower than 70° C.; and recycling a portion of said cooled reaction mixture at said lower temperature to said catalyst bed, in which the ratio of recycling is determined in accordance with the following equation (I) thereby avoiding the polymerization of propylene, reducing the loss of the activity of said catalyst, and improving both the catalytic efficiency and the rate of reaction:

$$\frac{7.9A + 4.9}{3.7A^2 + 1.17A - 1} \leq X \qquad (I)$$

wherein the symbol X is the ratio by weight of the quantity of recycled current to the quantity of feed current and A is the molar ratio of acetic acid to propylene in the feed current.

2. The method of producing isopropyl acetate in accordance with the method of claim 1, wherein said feed current consists of acetic acid and a C$_3$ fraction obtained by catalytic cracking of petroleum.

3. A method for producing sec-butyl acetate comprising the steps of feeding acetic acid and one or both of 1-butene and 2-butene, both said acetic acid and said butene being in a liquid state and in cocurrent, through a continuous flow type fixed bed reactor containing a styrene-sulfonic acid type ion exchange resin catalyst and/or a phenol-sulfonic acid type ion exchange resin catalyst under the conditions that the molar ratio of acetic acid to said butene in the feed current is in the range of 1.0 to 2.0 and the LHSV of acetic acid relative to the catalyst is 0.1 to 10.0 while maintaining the temperature of the inlet of the catalyst bed in the range of 80° C. to 120° C.; cooling the obtained reaction mixture to a lower temperature which is lower than the temperature at the outlet of the catalyst bed and is not lower than 80° C.; and recycling a portion of said cooled reaction mixture at said lower temperature to said catalyst bed, in which the ratio of recycling is determined in accordance with the following equation (II) thereby avoiding the polymerization of butene, reducing the loss of the activity of said catalyst, and improving both the catalytic efficiency and the rate of reaction:

$$\frac{7.6A + 5.9}{3.6A^2 + 1.5A - 1} \leq X \quad (II)$$

wherein the symbol X is the ratio by weight of the quantity of recycled current to the quantity of feed current and A is the molar ratio of acetic acid to said butene in the feed current.

4. The method for producing sec-butyl acetate in accordance with the method of claim 3, wherein a fraction obtained by removing butadiene and isobutylene from a $C_4$ fraction that is obtained by thermally cracking naphtha, is used as the source of said butene.

5. A method for producing isopropyl acetate comprising the steps of feeding acetic acid and propylene both in a liquid state and in concurrent through a continuous flow type fixed bed reactor containing a styrene-sulfonic acid type ion exchange resin catalyst and/or a phenol-sulfonic acid type ion exchange resin catalyst under the conditions that the molar ratio of acetic acid to said propylene in the feed current is in the range of 1.0 to 2.0 and the LHSV of acetic acid relative to the catalyst is 0.1 to 10.0 while maintaining the temperature of the inlet of the catalyst bed in the range of 70° C. to 120° C.; cooling the obtained reaction mixture to a temperature not lower than 70° C.; and recycling a portion of said cooled reaction mixture to said catalyst bed, in accordance with the ratio defined by the following equation (I):

$$\frac{7.9A + 4.9}{3.7A^2 + 1.17A - 1} \leq X \quad (I)$$

wherein the symbol X is the ratio by weight of the quantity of recycled current to the quantity of feed current and A is the molar ratio of acetic acid to propylene in the feed current, wherein said recycled current is not subjected to another chemical reaction while being recycled.

6. The method of claim 4 wherein said feed current consists of acetic acid and a $C_3$ fraction obtained by catalytic cracking of petroleum.

7. A method for producing sec-butyl acetate comprising the steps of feeding acetic acid and one or both of 1-butene and 2-butene, both said acetic acid and said butene being in a liquid state and in concurrent, through a continuous flow type fixed bed reactor containing a styrene-sulfonic acid type ion exchange resin catalyst and/or a phenol-sulfonic acid type ion exchange resin catalyst under the conditions that the molar ratio of acetic acid to said butene in the feed current is in the range of 1.0 to 2.0 and the LHSV of acetic acid relative to the catalyst is 0.1 to 10.0 while maintaining the temperature of the inlet of the catalyst bed in the range of 80° C. to 120° C.; cooling the obtained reaction mixture to a temperature not lower than 80° C.; and recycling a portion of said cooled reaction mixture to said catalyst bed, in accordance with the ratio defined by the following equation (II):

$$\frac{7.6A + 5.9}{3.6A^2 + 1.5A - 1} \leq X \quad (II)$$

wherein the symbol X is the ratio by weight of the quantity of recycled current to the quantity of feed current and A is the molar ratio of acetic acid to said butene in the feed current, wherein said recycled current is not subjected to another chemical reaction while being recycled.

8. The method of claim 7 wherein a fraction obtained by removing butadiene and isobutylene from a $C_4$ fraction that is obtained by thermally cracking naphtha is used as the source of said butene.

* * * * *

UNITED STATES PATENT AND TRADEMARK OFFICE
CERTIFICATE OF CORRECTION

PATENT NO. : 5,457,228
DATED : October 10, 1995
INVENTOR(S) : Yuichi Tokumoto, et al.

It is certified that error appears in the above-indentified patent and that said Letters Patent is hereby corrected as shown below:

Column 1, line 35: "$CH_2\!-\!CH_3$" should read -- $CH_3$ --

Signed and Sealed this

Eleventh Day of June, 1996

Attest:

BRUCE LEHMAN

Attesting Officer

Commissioner of Patents and Trademarks